United States Patent [19]

Arita et al.

[11] Patent Number: 4,822,822

[45] Date of Patent: Apr. 18, 1989

[54] BENZYLAMINE DERIVATIVES, AND USE THEREOF

[75] Inventors: Masanobu Arita; Kiyoshi Arai, both of Yokohama; Nobuo Komoto, Mitaka; Setsuko Hirose, Tachikawa; Takeshi Sekine, Hiratsuka, all of Japan

[73] Assignee: Mitsui Toatsu Chemicals, Inc., Tokyo, Japan

[21] Appl. No.: 923,274

[22] Filed: Oct. 27, 1986

[30] Foreign Application Priority Data

Nov. 1, 1985 [JP] Japan .................................. 60-243831

[51] Int. Cl.⁴ ...................... A01N 33/02; C07C 87/28
[52] U.S. Cl. .................................... 514/655; 564/387; 71/003
[58] Field of Search ............... 564/374, 375, 376, 387; 514/655, 895

[56] References Cited

U.S. PATENT DOCUMENTS 3,202,711 8/1965 Fruhstorfer et al. ............... 564/316
4,680,291 7/1987 Hamberger et al. ............ 564/387 X

FOREIGN PATENT DOCUMENTS 0000896 7/1979 European Pat. Off. ............. 564/387
0164697 12/1985 European Pat. Off. ............. 564/387
5089352 12/1973 Japan ................................. 564/387
790202 2/1958 United Kingdom ................ 564/387

Primary Examiner—Robert V. Hines
Attorney, Agent, or Firm—Fisher, Christen & Sabol

[57] ABSTRACT

Benzylamine derivatives having the general formula

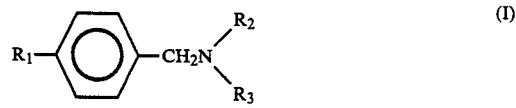

(I)

wherein $R_1$ is an iso-propyl or tert-butyl group, $R_2$ is a group of the formula:

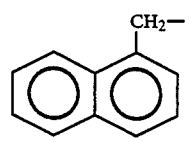

and $R_3$ is a lower alkyl or lower alkenyl group, or its acid addition salt. These derivatives are useful for the treatment of animal epidemics or infectious diseases induced by fungi as an antimycotic agent for humans and animals, for the control of plant diseases as an agricultural fungicide, and for the control of fungi and bacteria in industrial materials or products as an industrial fungicide.

6 Claims, No Drawings

BENZYLAMINE DERIVATIVES, AND USE THEREOF

BACKGROUND OF THE INVENTION

1. Field of the Invention

This invention relates to benzylamine derivatives represented by the general formula (I)

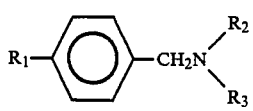

wherein
R₁ represents an alkyl group,
R₂ represents a group of the formula

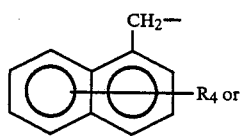

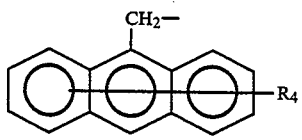

in which
R₄ represents a hydrogen atom, a lower alkyl group or a halogen atom, and
R₃ represents an alkyl or alkenyl group, and acid addition salts thereof, and also to antimycotic agents for humans or animals, agricultural fungicides and industrial fungicides or microbicides comprising the above compounds as active ingredients.

2. Background Art

In recent years research and development of antibiotics such as cephalosporin derivatives has rapidly advanced, and many drugs effective for infections by Gram-positive or Gram-negative pathogenic bacteria have been developed and used. On the other hand, in spite of ever-increasing cases of mycosis which are difficult to cure, commercial antimycotic agents have not proved to be entirely satisfactory owing to insufficient effects or the occurrence of side-effects. It has been strongly desired therefore to develop antimycotic agents which are highly safe with reduced side-effects and can produce an outstanding therapeutic effect.

The same can be said with regard to agricultural and industrial fungicides. In recent years, many non-metallic fungicides have been developed in place of inorganic or organic heavy metal compounds having strong toxicity to humans and animals in spite of their high fungicidal effects. These non-metallic fungicides, however, give rise to many problems such as insufficient effects, insufficient residual effects, phytotoxicity and the development of resistant strains. In agriculture, it has been desired to develop fungicides which show outstanding effects against difficult-to-control plant diseases such as gray mold (*Botrytis cineria*) in cucumber, tomato, etc. in practical dosages and can be safely and easily used.

Only a few compounds, for example benzimidazole compounds (e.g., benomyl, thiophanate methyl) and dicarboximide compounds (e.g., procymidone) are known as agents effective for controlling gray mold. It was already reported in the stage of development work that strains resistant to these agents appeared. Furthermore, cross resistance is observed between benzimidazoles and dicarboximides. Hence, these chemicals cannot be easy-to-use fungicides with stable effects, and there has been a very great demand for the development of chemicals which are effective against this disease which causes a great deal of damage.

Non-metallic industrial fungicides have superseded inorganic or organic heavy metal compounds. But since their effects are limited to a particular range of microorganisms or the range of their application is limited, their fungicidal effects are not sufficient. Such industrial fungicides frequently cannot prevent contamination and biodeterioration of industrial materials and products. For example, benzimidazole-type compounds, which are regarded as the best non-metallic fungicides, exhibit excellent fungicidal activity against such fungi as *Aspergillus*, *Penicillium* and *Trichoderma* by an agar dilution method which occur in paints, pastes, wooden and bamboo products, textiles, etc. and degrade them, but show no fungicidal activity against *Alternaria* and *Mucor* which occur on the coated surfaces of emulsion paints, artificial leathers, wall cloths, etc. These benzimidazole compounds show no activity against bacteria. Moreover, their effects cannot be expected in practical dosages (100 to 500 ppm) in many situations of actual use, for example, in anti-fungal treatment of paint films, wall trimming materials and wooden and bamboo products. It has been desired therefore to develop industrial fungicides or microbiocides which exhibits an outstanding effect in practical dosages and yet are safe and easy to use.

Benzylamine derivatives of the following general formula (IX)

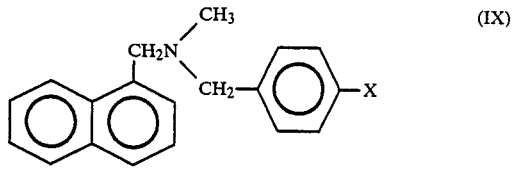

wherein X represents a hydrogen or chlorine atom or a methoxy group, which are similar to the compounds of this invention, are disclosed in J. Org. Chem., 12, 760 (1947). This paper reports the results obtained by screening various arylmethylamine derivatives for antimalarial activity. The paper states that no activity is noted in compounds of general formula (IX). Furthermore, it fails to describe any biological activities including antimycotic activity of the compounds (IX).

BROAD DESCRIPTION OF THE INVENTION

It is an object of this invention to overcome the defects of the conventional drugs or chemicals described above, and to provide antimycotic agents, and agricultural and industrial fungicides having excellent properties.

It is a specific object of this invention to provide an antimycotic agent for humans and animals which can be used safely with reduced side-effects and produce an outstanding therapeutic effect; an agricultural fungicide which produces an accurate control effect without phytotoxicity to plants; and an industrial fungicide which completely controls a variety of fungi occurring in industrial materials and products and causing contamination over an extended period of time with a high degree of safety.

In order to achieve the above objects, the present inventors have studied a number of benzylamine derivatives, and have now found that benzylamine derivatives represented by the following general formula (I)

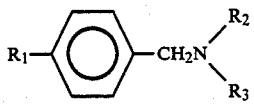 (I)

wherein
R₁ represents an alkyl group,
R₂ represents a group of the formula

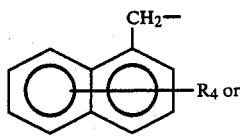 (II-a)

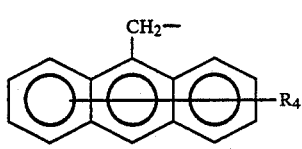 (II-b)

in which
R₄ represents a hydrogen atom, a lower alkyl group or a halogen atom, and
R₃ represents an alkyl or alkenyl group, and acid addition salts thereof have excellent antifungal activity and a wide range of antifungal spectrum against fungi. The present inventors have also found that the compounds of this invention have an excellent control effect against plant pathogens.

Thus, according to this invention, there are provided a benzylamine derivative represented by the following general formula (I)

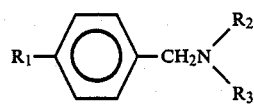 (I)

wherein
R₁ represents an alkyl group,
R₂ represents a group of

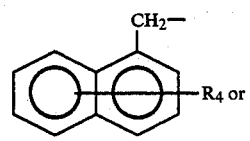 (II-a)

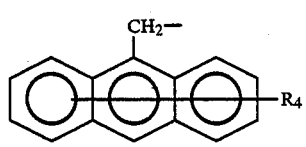 (II-b)

in which

R₄ represents a hydrogen atom, a lower alkyl group or a halogen atom, and
R₃ represents an alkyl or alkenyl group, and its acid addition salt. This invention also includes a process for producing a benzylamine derivative represented by the general formula (I)

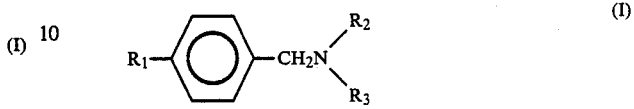 (I)

wherein
R₁ represents an alkyl group,
R₂ represents a group of formula

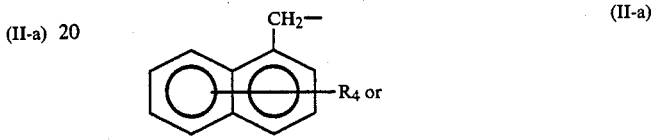 (II-a)

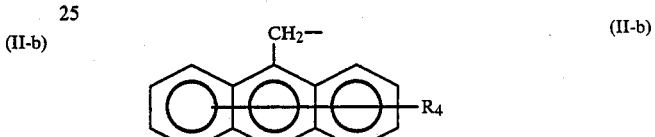 (II-b)

in which
R₄ represents a hydrogen atom, a lower alkyl group or a halogen atom, and
R₃ represents an alkyl or alkenyl group, which comprises reacting a compound represented by the general formula (III)

$$R_2\text{-NH-}R_3 \quad \text{(III)}$$

wherein R₂ and R₃ are as defined above, with a compound represented by the general formula (IV)

 (IV)

wherein
R₁ is as defined and
X represents a reactive residue, or reacting a compound represented by the general formula (V)

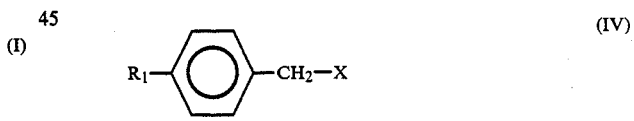 (V)

wherein R₁ and R₃ are as defined, with a compound represented by the general formula (VI)

$$X\text{-}R_2 \quad \text{(VI)}$$

wherein X and R₂ are as defined, or reacting a compound represented by the general formula (VII)

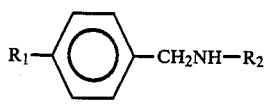 (VII)

wherein R₁ and R₂ are as defined above, with a compound represented by the general formula (VIII)

X-R₃ (VIII)

wherein R₃ and X are as defined above; an antimycotic agent for humans or animals comprising a benzylamine derivative represented by the general formula (I)

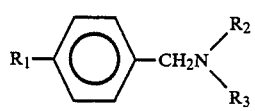 (I)

wherein R₁, R₂ and R₃ are as defined hereinabove, or its acid addition salt as an active ingredient. This invention further includes an industrial or agricultural fungicide comprising a benzylamine derivative represented by the general formula (I)

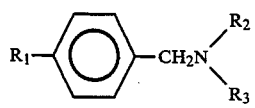 (I)

wherein R₁, R₂ and R₃ are as defined above, or its acid addition product as an active ingredient; a method of treating an epidemic or an infectious disease induced by a fungus, which comprises applying to an animal requiring therapy an effective amount of benzylamine derivative represented by the following general formula (I)

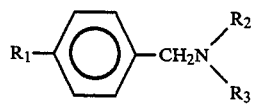 (I)

wherein R₁, R₂ and R₃ are as defined above, or its chemotherapeutically acceptable acid addition salt. This invention also includes a method of controlling a plant which comprises applying an effective amount of a benzylamine derivative represented by the general formula

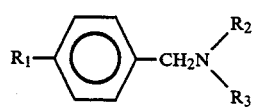 (I)

wherein R₁, R₂ and R₃ are as defined, or its acid addition salt to the plant. This invention also includes and a method of controlling fungi and bacteria which comprises treating industrial materials or industrial products with an effective amount of a benzylamine derivative represented by the general formula (I)

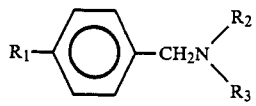 (I)

wherein R₁, R₂ and R₃ are as defined above, or its acid addition salt, or incorporating an effecitve amount of the benzylamine derivative in the industrial material or product.

The compounds of this invention represented by general formula (I) are novel compounds. Specifically, in general formual (I), R₁ represents an alkyl group such as methyl, ethyl, n-propyl, isopropyl, n-butyl, isobutyl, tert-butyl, n-pentyl, isopentyl, neopentyl, 1,1-dimethylpropyl, n-hexyl, 1-methylpentyl, 1,1-dimethylbutyl, n-heptyl, 1-methylhexyl, n-octyl and 1-methylheptyl; R₃ represents an alkyl group such as methyl, ethyl, n-propyl, isopropyl, n-butyl, isobutyl, tert-butyl, n-pentyl, isopentyl and neopentyl, or an alkenyl group such as vinyl, allyl, 2-methyl-2-propenyl and 2-methyl-1-propenyl; and R₄ represents a hydrogen atom, a lower alkyl group such as methyl or ethyl, or a halogen atom.

The compounds of formula (I) can be produced through any of routes (A), (B) and (C) shown below.

 (A)

(III) (IV)

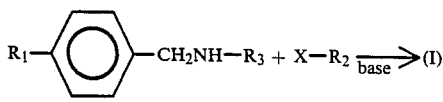 (B)

(V) (VI)

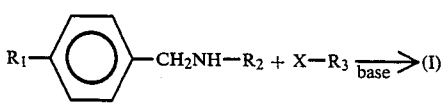 (C)

(VII) (VIII)

In the formulae, R₁, R₂ and R₃ have the aforesaid meanings, and X represents a reactive residue (such as a halogen atom or an ester residue such as benzenesulfonyl and tosyl.

In route (A), the compounds of formulae (III) and (IV) are reacted. In route (B), the compounds of formulae (V) and (VI) are reacted. In route (C), the compounds of formulae (VII) and (VIII) are reacted. All these reactions are performed in an inert solvent in the presence of a basic substance.

Examples of suitable inert solvents that can be used in these reactions include lower alcohols such as methanol and ethanol (as required, as a mixture with water); aromatic hydrocarbons such as benzene, toluene and xylene; halogenated hydrocarbons such as chloroform, carbon tetrachloride, monochlorobenzene and dichlorobenzene; ketones such as acetone, dimethyl ethyl ketone and methyl isobutyl ketone; ethers such as diethyl ether, dioxane and tetrahydrofuran; and aprotic polar solvents such as dimethylformamide, dimethyl sulfoxide and dimethylimidazolidinone. Examples of the base in the above reactions include inorganic bases such as sodium carbonate, potassium carbonate, sodium hydrogen carbonate, potassium hydrogen carbonate, sodium hydroxide, potassium hydroxide, sodium hydride, potassium hydride, sodium alcoholate and ammonia; and organic bases such as trimethylamine, triethylamine and pyridine. The reaction temperature is from 0° C. to the boiling point of the reaction mixture, preferably from room temperature to 60° C. The reaction time may be long, but usually a period of 1 to 6 suffices.

As required, the compound obtained by this invention is converted in a customary manner to an acid addition salt. Acids which can form such an acid addition salt include, for example, organic acids such as acetic acid, citric acid, tartaric acid, malic acid, oxalic acid, fumaric acid, maleic acid, succinic acid, naphthalene-1,5-disulfonic acid, naphthalene-2,7-disulfonic acid, and p-toluenesulfonic acid; and inorganic acids such as hydrohalic acids, sulfuric acid, nitric acid and phosphoric acid.

The compounds of formula (I) of this invention have excellent fungicidal activity against a wide range of fungi including animal parasitic fungi and plant pathogenic fungi, and can therefore be applied to protect animals, plants, and industrial materials and products from an attack of various fungi.

The compounds of this invention can be used in the form of a free base or a chemotherapeutically acceptable acid addition salt. Usually, however, they are formulated and used according to specific uses as shown below.

For use as an antimycotic agent for humans or animals, the compound of this invention may be orally administered as a mixture with a chemotherapeutically acceptable diluent and carrier and if further required with other vehicles for forming tablets or capsules. It can also be applied topically in an ordinary form such as an ointment or a cream. Such formulations can be generally prepared in accordance with customary methods for formulation. The dosage for a human adult is, for example 100 to 2,000 mg per day by oral administration.

For use as an industrial or agricultural fungicide, the compound of the invention can be used ordinarily as a formulation held on a carrier, such as an oil-soluble agent, an emulsifiable concentrate, a paste, a dust, a wettable powder and an aerosol.

In the formulation of the compounds of this invention, liquid carriers which do not react with the active component can be used. Examples include water, alcohols such as methanol, ethanol, ethylene glycol and propylene glycol, ketones such as acetone and methyl ethyl ketone, ethers such as dioxane, tetrahydrofuran, Cellosolve, diethylene glycol monomethyl ether, and diethylene glycol monoethyl ether, aliphatic hydrocarbons such as kerosene and gasoline, aromatic hydrocarbons such as benzene, toluene and xylene, halogenated hydrocarbons such as chloroform and dichloroethane, acid amides such as dimethylformamide, esters such as ethyl acetate, organic bases such as pyridine, and nitriles such as acetonitrile. Inorganic solid carriers such as clay, talc, bentonite, kaolin and white carbon, and gaseous carriers such as dimethyl ether or Freon gas can also be used.

As required, ionic or nonionic surface-active agents and polymeric compounds such as polyvinyl acetate and methyl cellulose can be used as auxiliary agents for increasing the formulation effect. The industrial or agricultural fungicide can also be used in admixture, or in combination, with other agricultural chemicals such as an insecticide, an acaricide, a fungicide, a herbicide, and a plant growth regulator, a perfume, or another industrial antifungal or antibacterial agent.

DETAILED DESCRIPTION OF THE INVENTION

The following Examples, Formulation Examples and Test Examples illustrate the present invention in greater detail. It should be understood however that these examples in no way limit the scope of the invention.

First, the production of the compounds of this invention will be specifically described.

EXAMPLE 1

Route A

Production of N-methyl-N-(4'-t-butylbenzyl)-1-naphthylmethylamine

N-methyl-1-naphthylmethylamine hydrochloride (2.1 g; 0.01 mole) was dissolved in 50 ml of dry dimethylformamide, and 3.71 g (0.035 mole) of anhydrous sodium carbonate was added. The mixture was stirred at room temperature, and 2.49 g (0.011 mole) of p-t-butylbenzyl bromide was added. The mixture was reacted at 30° to 40° C. for 5 hours. Ice water was added to the reaction mixture, and the mixture was extracted with toluene. The organic layer was washed with water, and toluene was evaporated. The residue was chromatographed on a silica gel column, and eluted with 5% ethyl acetate/n-hexane. The eluate was concentrated to give 2.98 g (yield 94%) of an oily substance.

EXAMPLE 2

Production of N-methyl-N-(4'-t-butylbenzyl)-1-naphthylmethylamine hydrochloride

Hydrochloric acid/ethanol was added to 1.0 g of the compound obtained in Example 1, and the mixture was concentrated. The residue was recrystallized from methanol/acetic acid to give 0.95 g of the desired hydrochloride having a melting point 200° to 202° C.

EXAMPLE 3

Route B

Production of N-(isopropyl)-N-(4'-t-butylbenzyl)-1-naphthylmethylamine 2.1 g (0.01 mole) of N-(isopropyl)-4-t-butylbenzylamine was dissolved in 50 ml of dry dimethylformamide, and 1.6 g (0.015 mole) of anhydrous sodium carbonate was added. While the mixture was stirred at room temperature, 1.94 g (0.011 mole) of 1-(chloromethyl)-naphthalene was added. The mixture was reacted at 30° to 40° C. for 6 hours. Ice water was added to the reaction mixture, and the mixture was extracted with toluene. The organic layer was washed with water and then toluene was evaporated. The residue was chromatographed on a silica gel column and eluted with 5% ethyl acetate/n-hexane. The eluate was concentrated to give 3.17 g (yield 92%) of an oily substance.

EXAMPLE 4

Production of N-(isopropyl)-N-(4'-t-butylbenzyl)-1-naphthylmethylamine hydrochloride Hydrochloric acid/ethanol was added to 1.0 g of the compound obtained in Example 3, and the mixture was concentrated. The residue was recrystallized from methanol/acetic acid to give 0.97 g of the desired hydrochloride having a melting point of 82° to 85° C.

EXAMPLE 5

Route C

Production of N-allyl-N-(4'-t-butylbenzyl)-1-naphthylmethylamine 3.03 g (0.01 mole) of N-(4'-t-butylbenzyl)-1-naphthylmethylamine was dissolved in 50 ml of dry dimethylformamide, and 1.6 g (0.015 mole) of anhydrous sodium carbonate was added. With continued stirring at room temperature, 0.84 g (0.011 mole) of allyl chloride was added, and the mixture was reacted at 30° to 40° C. for 5 hours. The reaction mixture was mixed with ice water and extracted with toluene. The organic layer was washed with water, and toluene was evaporated. The residue was chromatographed on a silica gel column, and eluted with 5% ethyl acetate/n-hexane. The eluate was concentrated to give 3.26 g (yield 95%) of an oily substance.

EXAMPLE 6

Route A

Production of N-methyl-N-(4'-isopropylbenzyl)-1-naphthylmethylamine 1.71 g (0.01 mole) of N-methyl-1-naphthylmethylamine was dissolved in 30 ml of tetrahydrofuran, and 1.2 g (0.012 mole) of triethylamine was added. With stirring at room temperature, 1.85 g (0.011 mole) of p-isopropylbenzyl chloride was added, and the mixture was reacted at room temperature for 6 hours. The reaction mixture was filtered, and the solvent was removed under reduced pressure. The residue was distributed between ether and a saturated aqueous solution of sodium hydrogen carbonate, and the organic layer was collected. The organic layer was washed with water, dried over sodium sulfate and then concentrated under reduced pressure. The residue was chromatographed on a silica gel column and eluted with 4% ethyl acetate/n-hexane. The eluate was concentrated to give 2.82 g (yield 93%) of an oily substance.

EXAMPLE 7

Production of N-methyl-N-(4'-isopropylbenzyl)-1-naphthylmethylamine hydrochloride Hydrochloric acid/ethanol was added to 1.0 g of the compound of Example 6, and the mixture was concentrated. The residue was recrystallized from methanol/ethyl acetate to give 0.86 g of the desired hydrochloride having a melting point of 178° to 180° C.

EXAMPLE 8

Route B

Production of N-methyl-N-(4'-isopropylbenzyl)-1-(2-methylnaphthalene)methylamine 1.63 g (0.01 mole) of N-methyl-4-isopropylbenzylamine was dissolved in 60 ml of acetone, and 1.6 g (0.015 mole) of anhydrous sodium carbonate was added. With continued stirring at room temperature, 2.1 g (0.011 mole) of 1-chloromethyl-2-methylnaphthalene was added. The mixture was reacted at 30° to 40° C. for 6 hours. The reaction mixture was filtered, and the solvent was removed under reduced pressure. The residue was distributed between ether and a saturated aqueous solution of sodium hydrogen carbonate, and the organic layer was collected. The solvent was removed under reduced pressure, and hydrochloric acid/ethanol was freshly added. The mixture was concentrated, and the residue was recrystallized from methanol/ethyl acetate to give white crystals. The white crystals were distributed between ether and a 1N aqueous solution of sodium hydroxide, and the organic layer was separated. The organic layer was fully washed with water, dried over sodium sulfate and concentrated under reduced pressure to give 2.82 g (yield 89%) of the desired oily substance.

EXAMPLES 9–10

In the same way as in Example 6 or 7, the compounds given in Table 1 were obtained.

EXAMPLE 11

Route A

Production of N-methyl-N-(4'-t-butylbenzyl)-9-anthrylmethylamine 2.2 g (0.01 mole) of N-methyl-9-anthrylmethylamine was dissolved in 40 ml of toluene, and 1.7 g (0.012 mole) of anhydrous potassium carbonate was added. With continued stirring at room temperature, 2.49 g (0.011 mole) of p-t-butylbenzylbromide was added, and the mixture was reacted at 40° to 50° C. for 4 hours. The reaction mixture was mixed with ice water, and distributed. The organic layer was washed with water, and toluene was evaporated. The residue was chromatographed on a silica gel column, and eluted with 4% ethyl acetate/n-hexane. The eluate was concentrated to give 3.3 g (yield 91%) of an oily substance.

EXAMPLES 12–13

In the same way as in Example 7 or 11, the comounds given in Table 1 were obtained.

TABLE 1

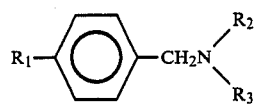

(I)

| Example | R₁ | R₂ | R₃ | Salt kind | Elemental analysis or melting point (°C.) | | C | H | N | NMR $\delta^{CDCl_3}_{TMS}$ (ppm) |
|---|---|---|---|---|---|---|---|---|---|---|
| 1 | (CH₃)₃C— | naphthalen-1-ylmethyl (CH₂-naphthyl) | —CH₃ | — | Calculated (%)<br>Found (%) | | 87.02<br>87.11 | 8.57<br>8.52 | 4.41<br>4.37 | 1.32(9H,s), 2.22(3H,s), 3.59 (2H,s), 3.95(2H,s), 7.72–7.86 (10H,m), 8.23(1H,m) |
| 2 | " | " | " | HCl | m.p. 200–202 | | | | | |
| 3 | " | " | —CH(CH₃)₂ | — | Calculated (%)<br>Found (%) | | 86.90<br>86.96 | 9.04<br>9.00 | 4.06<br>3.97 | 1.08(3H,s), 1.15(3H,s), 1.28 (9H,s), 3.01(1H,m), 3.58(2H,s) 4.02(2H,s), 7.16–7.84(10H,m), 8.21(1H,m) |
| 4 | " | " | " | HCl | m.p. 82–85 | | | | | |
| 5 | " | " | —CH₂CH=CH₂ | — | Calculated (%)<br>Found (%) | | 87.41<br>87.50 | 8.51<br>8.45 | 4.08<br>4.01 | 1.32(9H,s), 3.12(2H,d,J=7Hz), 3.60(2H,s), 4.01(2H,s), 5.23 (2H,m), 5.98(1H,m), 7.20–7.86 (10H,m), 8.22(1H,m) |
| 6 | —CH(CH₃)₂ | " | —CH₃ | — | Calculated (%)<br>Found (%) | | 87.08<br>87.05 | 8.30<br>8.24 | 4.62<br>4.56 | 1.24(6H,d,J=8Hz), 2.21(3H,s), 2.89(1H,m), 3.58(2H,s), 3.92(2H,s), 7.16–7.89(10H,m), 8.26(1H,m) |
| 7 | " | " | " | HCl | m.p. 178–180 | | | | | |
| 8 | " | 2-methyl-naphthalen-1-ylmethyl | " | — | Calculated (%)<br>Found (%) | | 87.02<br>87.18 | 8.57<br>8.50 | 4.41<br>4.36 | 1.25(6H,d,J=7Hz), 2.21(3H,s) 2.59 (3H,s), 2.88(1H,m), 3.56(2H,s), 3.96 (2H,s), 7.14–7.82(9H,m), 8.26(1H,m) |
| 9 | (CH₃)₃C— | " | " | — | Calculated (%)<br>Found (%) | | 86.96<br>87.04 | 8.82<br>8.75 | 4.22<br>4.19 | 1.34(9H,s), 2.22(3H,s), 2.62(3H,s), 3.60(2H,s), 3.99(2H,s), 7.18–7.82 (9H,m), 8.26(1H,m) |
| 10 | " | " | " | HCl | m.p. 207–209 | | | | | |
| 11 | " | anthracen-9-ylmethyl | " | — | Calculated (%)<br>Found (%) | | 88.24<br>88.29 | 7.95<br>7.88 | 3.81<br>3.80 | 1.36(9H,s), 2.38(3H,s), 3.98(2H,s) 4.80(2H,s), 7.35–7.60(8H,m), 7.90–8.06(2H,m), 8.20–8.46(3H,m) |
| 12 | " | " | " | HCl | m.p. 198.5–199.5 | | | | | |
| 13 | —CH(CH₃)₂ | " | " | — | Calculated (%)<br>Found (%) | | 88.34<br>88.40 | 7.70<br>7.70 | 3.96<br>3.91 | 1.24(6H,d,J=7Hz), 2.24(3H,s), 2.92(1H,m), 3.67(2H,s), 4.46(2H,s), 7.08–7.56(8H,m), 7.90–8.02(2H,m), 8.22–8.46(3H,m) |
| 14 | (CH₃)₃C— | 4-chloronaphthalen-1-ylmethyl | " | — | Calculated (%)<br>Found (%) | | 78.50<br>78.56 | 7.45<br>7.38 | 3.98<br>3.91 | 1.33 (9H,s), 2.20(3H,s), 3.57(2H,s) 3.89(2H,s), 7.19–7.63(8H,m), 8.20–8.37(2H,m) |

The following Formulation Examples illustrate the composition of this invention more specifically.

FORMULATION EXAMPLE 1

| | |
|---|---|
| Compound 1 of the invention | 20 parts |
| Sorpol AC-3153 (surface-active agent produced by Toho Chemical Industry Co., Ltd.) | 10 parts |
| Propylene glycol | 10 parts |
| Water | 60 parts |

The above ingredients were mixed uniformly to obtain a suspension.

| FORMULATION EXAMPLE 2 | |
|---|---|
| Compound 6 of the invention | 20 parts |
| Noigen EA-97 (surface-active agent produced by Daiichi Industrial Chemicals Co., Ltd.) | 8 parts |
| Emal 10 (surface-active agent produced by Kao Co., Ltd.) | 2 parts |
| Water | 70 parts |

The above ingredients were uniformly mixed to obtain a suspension.

| FORMULATION EXAMPLE 3 | |
|---|---|
| Compound 2 of the invention | 20 parts |
| Emal 10 | 5 parts |
| Emulgen 920 (surface-active agent produced by Kao Co., Ltd.) | 5 parts |
| Clay | 70 parts |

The above ingredients were pulverized and uniformly mixed to obtain a wettable powder.

| FORMULATION EXAMPLE 4 | |
|---|---|
| Compound 9 of the invention | 40 parts |
| Diskzol BP-158 (surface-active agent produced by Daiichi Industrial Chemicals, Co., Ltd.) | 7 parts |
| Amiet 105 (surface-active agent produced by Kao Co., Ltd.) | 13 parts |
| Xylene | 40 parts |

The above ingredients were uniformly mixed to obtain an emulsifiable concentrate.

| FORMULATION EXAMPLE 5 | |
|---|---|
| Compound 11 of the invention | 40 parts |
| Toho DB-100 (surface-active agent produced by Toho Chemical Industry Co., Ltd.) | 12 parts |
| Noigen EA-140 (surface-active agent produced by Daiichi Industrial Chemicals Co., Ltd.) | 8 parts |
| Xylene | 40 parts |

The above ingredients were uniformly mixed to obtain an emulsifiable concentrate.

| FORMULATION EXAMPLE 6 | |
|---|---|
| Compound 4 of the invention | 2 parts |
| Calcium stearate | 1 part |
| Powdery silica gel | 1 part |
| Diatomaceous earth | 20 parts |
| CARPPLEX ® (terra alba) | 30 parts |
| Talc | 46 parts |

The above ingredients were uniformly pulverized and mixed to obtain a dust.

TEST EXAMPLE 1

Test for evaluating antifungal activity (1)

The antifungal activity was evaluated by the agar dilution method. Specifically, each of the compounds of this invention was mixed with a potato dextrose agar medium in a serial concentration of 0.16 to 100 ppm. After thorough mixing, the mixture was poured into a Petri dish to prepare an agar plate. After the agar solidified, a pure culture of each of the test microorganisms indicated below was inoculated in the agar plate, and cultivated at 25° C. for 7 days. The minimum concentration of the test compound in the medium at which the inoculated microorganism did not grow was determined, and shown in Table 2 as a minimum inhibitory concentration (MIC, ppm).

The test microorganisms were as follows:

| Microorganism | Abbreviated designation |
|---|---|
| *Aspergillus niger* | A.n. |
| *Penicillium citrinum* | P.c. |
| *Cladosporium herbarum* | C.h. |
| *Chaetomium globosum* | C.g |
| *Trichoderma viride* | T.v. |
| *Aureobasidium pullulans* | A.p. |
| *Alternaria alternata* | A.a. |

As a comparative compound, there was used 2-(4-thiazolyl)-benzimidazole (TBZ for short) which is known to have a particularly stable effect among benzimidazole compounds regarded as best among non-metallic industrial fungicides now in use.

Known compound, N-methyl-N-(4-methoxybenzyl)-1-naphthylmethylamine having a similar structure to the compound of this invention was also tested as a referential compound.

TABLE 2

| | MIC (ppm) Test organism | | | | | | |
|---|---|---|---|---|---|---|---|
| Test compound | A.n. | P.c. | C.h. | C.g. | T.v. | A.p. | A.a. |
| Compound 1 | 0.8 | ≦0.16 | ≦0.16 | 0.8 | 0.8 | ≦0.16 | 0.8 |
| Compound 2 | ≦0.16 | ≦0.16 | ≦0.16 | 0.8 | 0.8 | 0.8 | 0.8 |
| Compound 3 | 0.8 | ≦0.16 | ≦0.16 | 100 | 20 | 4.0 | ≦0.16 |
| Compound 4 | 0.8 | 0.8 | 0.8 | 100 | 100 | 4.0 | 4.0 |
| Compound 5 | 0.8 | ≦0.16 | ≦0.16 | 100 | 100 | 100 | 0.8 |
| Compound 6 | 4.0 | 0.8 | 4.0 | 4.0 | 20 | 4.0 | ≦0.16 |
| Compound 7 | 4.0 | 0.8 | 4.0 | 20 | 20 | 4.0 | 20 |
| Compound 8 | 4.0 | 0.8 | 4.0 | 20 | 20 | 4.0 | 4.0 |
| Compound 9 | ≦0.16 | ≦0.16 | 0.8 | 0.8 | 4.0 | 4.0 | 0.8 |
| Compound 10 | 0.8 | 0.8 | 0.8 | 0.8 | 20 | 4.0 | 0.8 |
| Comparative compound TBZ(*1) | 4.0 | 0.8 | 4.0 | 4.0 | 4.0 | 0.8 | 100< |
| Referential compound A(*2) | 100< | 100< | 100< | 100< | 100< | 100< | 100< |

(*1) TBZ; 2-(4-thiazolyl)-benzimidazole
(*2) N—methyl-N—(4'methoxybenzyl)-1-naphthylmethylamine [J. Org. Chem., 12, 760 (1947)]

It is clear from Table 2 that the compounds of this invention have strong antifungal activity against a variety of fungi which degrade industrial materials and products and cause a great deal of losses. They have specifically high antifungal activity against *Aspergillus niger* and *Penicillium citrinum* which cause hazards widely in paints, leathers, latex emulsions, oiling agents, communication devices and electrical devices. They also show high antifungal activity against *Alternalia alternata* against which the comparative compound TBZ did not at all show antifungal activity.

TEST EXAMPLE 2

Test for evaluation of antifungal activity (2)

The antifungal activity was evaluated by the paper disk method. A plate of malt-yeast extract-agar medium (pH 6.0) was prepared. Each of the test microorganisms 1 to 4 (as a spore suspension for the microorganisms 1, 3 and 4, and as a cell suspension for the miroorganism 2) was put in an amount of 0.2 ml (concentration $4 \times 10^7$ spores or cells/ml) in the plate, and spread by a spreader. A sterilized paper disk (diameter 8 mm) was placed on the plate, and 20 microliters of an acetone or water solution of each of the test compounds in various concentrations was injected into the paper disc, and the test microorganism was cultivated at 28° C. Five days later, the size of the inhibitory circular zone was measured, and the minimum inhibitory concentration, MIC (ppm), was determined. The results are shown in Table 3.

The test microorganisms were as follows:
*Aspergillus fumigatus* (HUT 2034),
*Candida albicans* (HUT 7105),
*Trichophyton mentagrophytes* (IFO 5929),
*Micorsporum gypseum* (IFO 8231).

Commercial Canestin (registered trademark) (clotrimazole) now widely used as an antimycotic agent was used as a comparative compound.

ficaceous against *Aspergillus fumigatus* which induces deep-seated mycosis.

The compounds of this invention also show antimycotic acitiviy in an in vivo test on the experimental dermal mycosis of guinea pigs. In this test, the compound of the invention was topically administered to a skin surface (as a solution in polyethylene glycol), or orally administered every day over 2 weeks from the 5th day after infection by trichophyton. The activity of the compound of the invention was observed in a concentration of 0.01 to 5% in topical administration and in a dose of 2 to 70 mg/kg in oral administration.

It is seen therefore that the compounds of this invention may be administered topically or orally when used as an antimycotic agent for humans or animals. The dose for a human adult may be 100 to 2,000 mg per day.

TEST EXAMPLE 3

Test for controlling gray mold on cucumber

Cucumber on the market was well washed, and cut to a size of 4 to 5 cm and dipped for about 2 to 3 minutes in a water dilution of a wettable powder of each of the test compounds prepared in accordance with Formulation Example 3 in a concentration of 500 ppm, and dried in the air. Air-dried cucumber pieces were put upstanding on the lawn of gray mold fungus which had been cultivated in a plate of PSA medium for 5 to 7 days, and then maintained at 18° C. for 4 to 5 days. The growth length of the lawn on the surface of cucumber pieces was examined, and the control index was calculated in accordance with the following equation. The results are shown in Table 4.

$$\text{Control index (\%)} = \left(1 - \frac{\text{Length of the lawn in a treated area}}{\text{Length of the lawn in a non-treated area}}\right) \times 100$$

TABLE 3

| | | | Test compound | | MIC(ppm) |
|---|---|---|---|---|---|
| Test organism | Compound 2 | Compound 4 | Compound 7 | Comparative compound (*1) | Referential compound B (*2) |
| *Asp. fumigatus* | 0.4 | 4.2 | 40 | 3.6 | 80 |
| *Can. albicans* | >100 | >100 | >100 | 8.0 | >100 |
| *Tri. mentagrophytes* | 0.009 | 0.8 | 0.06 | 4.0 | >100 |
| *Micro. gypseum* | 0.02 | 0.8 | 0.8 | 40.0 | 80 |

(*1) clotrimazole; canestin ® (a product of Bayer AG)

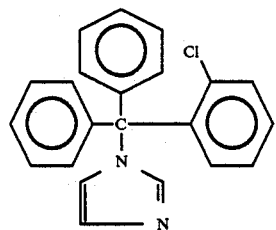

(*2) N—methyl-N—bnenzyl-1-naphthylmethylamine ]J. Org. Chem., 12, 760 (1947)]

It is apparent from Table 3 that the compounds of this invention show strong antifungal activity against fungi which are parasitic on humans or animals and induce mycoses. In particular, the compounds of the invention have much higher antifungal activity against *Trichophyton mentagrophytes* and *Microsporum gypseum,* which are dermatophytes, than clotrimazole, and are also ef- Topsin M which was commercially available and used generally as an effective gray mold controlling agent was used as a control chemical.

TABLE 4

| Test compound | Concentration (ppm) | Control index (%) |
|---|---|---|
| Compound 1 | 500 | 93 |

TABLE 4-continued

| Test compound | Concentration (ppm) | Control index (%) |
|---|---|---|
| Compound 2 | 500 | 100 |
| Compound 4 | 500 | 100 |
| Compound 7 | 500 | 88 |
| Compound 9 | 500 | 90 |
| Compound 10 | 500 | 100 |
| TOPSIN M (*) | 500 | 40 |
| Non-treated | — | 0 |

(*) TOPSIN M is (1,2-bis(3-methoxycarbonyl-2-thioureido)benzene) 70%

It is generally difficult to control gray mold, and a chemical which shows a high controlling effect has been desired. Table 4 clearly demonstrates that the compounds of this invention shows a higher control effect against gray mold than Topsin M.

As can be clearly seen from the foregoing statement, the compounds of this invention have an outstanding antifungal effect against animal parasitic fungi, plant pathogens and many fungi which degrade industrial materials and products, and can be effectively utilized for controlling many troubles and hazards which are induced by these fungi.

Accordingly, the compounds of the invention which can be utilized in medical, agricultural and industrial fields have a very high utilitarian value.

What is claimed is:

1. A benzylamine derivative having the general formula (I):

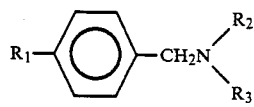

wherein $R_1$ is an iso-propyl or tert-butyl group, $R_2$ is a group of the formula:

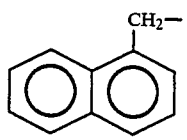

and $R_3$ is a lower alkyl or lower alkenyl group, or its acid addition salt.

2. An antimycotic agent for humans or animals comprising the benzylamine derivative having the general formula (I) in claim 1.

3. An industrial or agricultural fungicide comprising a benzylamine derivative having the general formula (I) in claim 1.

4. A method of treating an epidemic or an infectious disease induced by a fungus, which comprises administering to an animal requiring therapy an effective antimycotic amount of a benzylamine derivative having the general formula (I) in claim 1.

5. A method of controlling a plant disease which comprises applying to a plant an effective fungicidal amount of a benzylamine derivative having the general formula (I) in claim 1.

6. A method of controlling fungi and bacteria in an industrial material or product, which comprises treating the industrial material or product with an effective amount of a benzylamine derivative having the general formula (I) in claim 1.

* * * * *

Notice of Adverse Decision in Interference

In Interference No. 102,365, involving Patent No. 4,822,822, M. Arita, K. Arai, N. Komoto, S. Hirose, T. Sekine, BENZYLAMINE DERIVATIVES, AND USE THEREOF, final judgement adverse to the patentees was rendered Dec. 14, 1990, as to claims 1-4.

*(Official Gazette March 5, 1991)*